United States Patent
Karpeisky et al.

(10) Patent No.: US 9,334,300 B2
(45) Date of Patent: May 10, 2016

(54) VITAMIN B6 DERIVATIVES OF NUCLEOTIDES, ACYCLONUCLEOTIDES AND ACYCLONUCLEOSIDE PHOSPHONATES

(75) Inventors: Alexander Karpeisky, Lafayette, CO (US); Shawn Zinnen, Denver, CO (US); Murali Urlam, Sugar Land, TX (US); Vladimir Y. Vvedensky, San Diego, CA (US); Andrei P. Guzaev, Escondido, CA (US)

(73) Assignee: MBC PHARMA, INC., Aurora, CO (US)

(*) Notice: Subject to any disclaimer, the term of this patent is extended or adjusted under 35 U.S.C. 154(b) by 0 days.

(21) Appl. No.: 14/236,178

(22) PCT Filed: Aug. 1, 2012

(86) PCT No.: PCT/US2012/049181
§ 371 (c)(1),
(2), (4) Date: Jun. 3, 2014

(87) PCT Pub. No.: WO2013/019874
PCT Pub. Date: Feb. 7, 2013

(65) Prior Publication Data
US 2014/0329768 A1 Nov. 6, 2014

Related U.S. Application Data

(60) Provisional application No. 61/513,741, filed on Aug. 1, 2011, provisional application No. 61/620,861, filed on Apr. 5, 2012.

(51) Int. Cl.
| | |
|---|---|
| *A61K 31/70* | (2006.01) |
| *A01N 43/04* | (2006.01) |
| *C12N 5/00* | (2006.01) |
| *C12N 5/02* | (2006.01) |
| *C07H 19/048* | (2006.01) |
| *C07H 19/10* | (2006.01) |
| *C07D 213/76* | (2006.01) |
| *C07D 213/65* | (2006.01) |
| *C07H 19/12* | (2006.01) |
| *C07H 19/20* | (2006.01) |
| *C07H 19/23* | (2006.01) |
| *C07H 19/19* | (2006.01) |

(52) U.S. Cl.
CPC .............. *C07H 19/10* (2013.01); *C07D 213/65* (2013.01); *C07D 213/76* (2013.01); *C07H 19/12* (2013.01); *C07H 19/19* (2013.01); *C07H 19/20* (2013.01); *C07H 19/23* (2013.01)

(58) Field of Classification Search
CPC ........ C07H 19/23; C07H 19/19; C07H 19/12; C07H 19/10; C07H 19/20; C07D 213/65; C07D 213/76
See application file for complete search history.

(56) References Cited

U.S. PATENT DOCUMENTS

| | | |
|---|---|---|
| 4,032,625 A | 6/1977 | Subramanian et al. |
| 4,621,077 A | 11/1986 | Rosini |
| 5,130,304 A | 7/1992 | Binderup |
| 5,183,815 A | 2/1993 | Saari et al. |
| 5,358,941 A | 10/1994 | Bechard |
| 5,428,181 A | 6/1995 | Sugioka et al. |
| 5,434,143 A | 7/1995 | Spielvogel et al. |
| 5,488,041 A | 1/1996 | Barbier |
| 5,580,571 A | 12/1996 | Hostetler |
| 5,624,913 A | 4/1997 | Proctor et al. |
| 5,654,286 A | 8/1997 | Hostetler |
| 5,721,219 A | 2/1998 | Ingall |
| 5,760,013 A | 6/1998 | Hwu et al. |
| 5,900,410 A | 5/1999 | Hartmann |
| 6,004,939 A | 12/1999 | Chen et al. |
| 6,121,253 A | 9/2000 | Han et al. |
| 6,140,518 A | 10/2000 | Gallagher et al. |
| 6,214,812 B1 | 4/2001 | Karpeisky et al. |
| 6,605,603 B1 | 8/2003 | Roldan |
| 6,750,340 B2 | 6/2004 | Padioukova et al. |
| 6,896,871 B2 | 5/2005 | Karpeisky et al. |
| 6,929,797 B2* | 8/2005 | Mazess et al. ........... 424/195.11 |
| 7,285,658 B2 | 10/2007 | Cook et al. |
| 7,598,246 B2 | 10/2009 | Dixon et al. |
| 8,586,781 B2 | 11/2013 | Karpeisky et al. |

(Continued)

FOREIGN PATENT DOCUMENTS

| | | |
|---|---|---|
| CA | 2443857 | 6/2012 |
| DE | 19 18 282 A1 | 10/1969 |

(Continued)

OTHER PUBLICATIONS

Buxton et al. (1998) Abstracts of the Interscience Conference on Antimicrobial Agents and Chemotherapy 38:29 "Ciprofloxacin Conjugated to Bisphosphonate: Characterization fo Bone Affinity In Vitro" XP008043693.
Buxton et al. (2001) FASEB Journal 15(4):A587 "Novel Local Drug Delivery of Antibiotic-Bisphoophonate: Binding and Antibacterial Effects" XP008043697.
European Search Report from EP 10 18 3006 Dec. 13, 2010.
Fleish (1998) Endocrine Reviews 19(1):80-100 "Bisphosphonates: Mechanisms of Action".
Fujisaki et al. (1995) Proceedings of The International Symposium on Controlled Release of Bioactive Materials, 22:562-3 "Osteotropic Drug Delivery System(ODDS) Based on Bisphosphonic Prodrug".

(Continued)

*Primary Examiner* — Lawrence E Crane
(74) *Attorney, Agent, or Firm* — Brownstein Hyatt Farber Schreck LLP; Paul J. Prendergast; Cara Crowley-Weber

(57) ABSTRACT

Compounds and compositions are provided, as are methods of using them to treat infections, neoplastic disease, including pancreatic cancer, inflammatory disease, and pain. Such compounds are nucleotides, acyclonucleotides, and ANP phosphonates conjugated with forms and/or moieties of Vitamin $B_6$ for delivery past the cell membrane and into the cell.

10 Claims, 4 Drawing Sheets

(56) References Cited

U.S. PATENT DOCUMENTS

| | | | |
|---|---|---|---|
| 2008/0287396 | A1 | 11/2008 | Delorme |
| 2009/0239814 | A1 | 9/2009 | Manoharan et al. |
| 2014/0051625 | A1 | 2/2014 | Karpeisky et al. |
| 2014/0315851 | A1 | 10/2014 | Karpeisky et al. |

FOREIGN PATENT DOCUMENTS

| | | |
|---|---|---|
| EP | 0 100 718 | 2/1984 |
| EP | 0 512 844 | 11/1992 |
| EP | 2 260 852 | 1/2011 |
| WO | WO 88/00829 | 2/1988 |
| WO | WO 91/10646 | 7/1991 |
| WO | WO 96/40156 | 12/1996 |
| WO | WO 97/02279 | 1/1997 |
| WO | WO 98/35704 | 8/1998 |
| WO | WO 02/083150 | 10/2002 |
| WO | WO 2012/158811 | 11/2012 |
| WO | WO 2013/019874 | 2/2013 |

OTHER PUBLICATIONS

Gough et al. (1973) Journal of Medicinal Chemistry; 16(10):1188-1190 "Three New Adenosine Triphosphate Analogs, Synthesis and Effects on Isolated Gut".

Herczegh et al. (2002) J. Med. Chem. 45:2338-2341 "Osteoadsorptive bisphosphonate derivatives of fluoroquinolone antibacterials".

Hershey and Monro (1966) J. Mol. Biol. 18:68-76 "A Competitive Inhibitor of the GTP Reaction in Protein Synthesis".

Hosain et al. (1996) The Journal of Nuclear Medicine 37(1):105-107 "Targeted Delivery of Antineoplastic Agent to Bone: Biodistribution Studies of Technetium-99m-Labeled Gem-Bisphosphonate Conjugate of Methotrexate".

Houghton et al. (2008) J. Med. Chem. 51(21): 6955-6969 "Linking bisphosphonates to the free amino groups in fluoroquinolones: preparation of osteotropic prodrugs for the prevention of osteomyelitis".

International Search Report & Written Opinion with respect to PCT/US2012/049181 mailed Dec. 19, 2012.

Klein (1998) Journal of Cellular Biochemistry 68:186-194 "Structurally Different Bisphosphonates Exert Opposing Effects on Alkaline Phosphatase and Mineralization in Marrow Osteoprogenitors".

Lincosamides (2013) thefreedictionary.com Website: http://medical-dictionary.thefreedictionary.com/p/lincosamides, retrieved Mar. 20, 2013.

Murud et al. (1999) Nuclear Medicine and Biology 26(7):791-794 "Influence of Pretreatment with 3-Amino-1-Hydroxypropylidene-1,1-Bisphosphonate (APB) on Organ Uptake of 211At and 125I-Labeled Amidobisphosphonates in Mice".

Nancollas et al. (2006) Bone 38:617-627 "Novel Insights into Actions of Bisphosphonates on Bone: Differences in Interactions with Hydroxyapatite".

Ono et al. (1989) Molecular Pharmacology 35:578-583"Differential Inhibitory Effects of Several Pyrimidine 2', 3'-Dideoxynucleoside 5'-Triphosphates on the Activities of Reverse Transcriptase and Various Cellular DNA Polymerases".

Ora et al. (2008) Journal Organic Chemistry 73:4123-4130 "Bisphosphonate Derivatives of Nucleoside Antimetabolites: Hydrolytic Stability and Hydroxyapatite Adsorption of 5'-β,γ-Methylene and 5'-β,γ-(1-Hydroxyethylidene) Triphosphates of 5-Fluorouridine and ara-Cytidine".

Padyukova et al. (1999) Nucleosides & Nucleotides 18(4&5):1013-1014 "Synthesis and Properties of Novel NTP Derivatives".

Reddy et al. (2008) ChemMedChem 3: 1863-1868 "Bisphosphonated benzoxazinorifamycin prodrugs for the prevention and treatment of osteomyelitis".

Reinholz et al. (2002) Breast Cancer Research and Treatment 71:257-268 "Distinct mechanisms of bisphosphonate action between osteoblasts and breast cancer cells: identity of a potent new bisphosphonate analogue".

Renis (1973) Antimicrobial Agents and Chemotherapy 4(4):439-444 "Antiviral Activity of Cytarabine in Herpesvirus-Infected Rats".

Rocha et al. (2000) "Pyridoxine (vitamin B6) stimulates osteoblastic differentiation in vitro—Presentation No. SA213" Journal of Bone and Mineral Research XP-002609426.

Rogers et al. (1995) Molecular Pharmacology 47:398-402 "Structure-Activity Relationships of New Heterocycle-Containing Bisphosphonates as Inhibitors of Bone Resorption and as Inhibitors of Growth of Dictyostelium discoideum Amoebae".

Shirokova et al. (1999) Nucleosides and Nucleosides 18(4&5):1027-1028"Modified Nucloside 5'-Triphosphonates as a New Type of Antiviral Agents".

Shtil et al. (2000) Proceedings of the American Association for Cancer Research Annual Meeting 41:398 "Novel Bisphosphonate-Based Compounds for Circumventing Drug Resistance in the Bone-Targeting Human Tumor" XP-002319674.

Tanaka et al. (2008) Bioorganic and Medicinal Chemistry 16: 9217-9229 "Bisphosphonated fluoroquinolone esters as osteotropic prodrugs for the prevention of osteomyelitis".

Wermuth (1996) Academic Press, 203-237 (book chapter) "Molecular Variations Based on Isoteric Replacements".

Zhang and McCormick (1991) Proc. Natl. Acad. Sci. 88:10407-10410 "Uptake of N-(4'-Pyridoxyl)Amines and Release of Amines by Renal Cells: a Model for Transporter-Enhanced Delivery of Bioactive Compounds".

Sofia, M.J. (2011) "Nucleotide Prodrugs for HCV Therapy," Antiviral Chemistry & Chemotherapy, 22:23-49.

Tagaya et al. (1985) "A New Affinity Labeling Reagent for the Active Site of Glycogen Synthase," Journal of Biological Chemistry, 260(11):6870-8676.

International Search Report for International Application No. PCT/US2012/049181 mailed Dec. 19, 2012 (3 pages).

\* cited by examiner

US 9,334,300 B2

VITAMIN B6 DERIVATIVES OF NUCLEOTIDES, ACYCLONUCLEOTIDES AND ACYCLONUCLEOSIDE PHOSPHONATES

This application is a National Stage Application of PCT/US2012/049181, filed 1 Aug. 2012, which claims benefit of U.S. Provisional Ser. No. 61/513,741, filed 1 Aug. 2011 and U.S. Provisional Ser. No. 61/620,861, filed 5 Apr. 2012 and which applications are incorporated herein by reference. To the extent appropriate, a claim of priority is made to each of the above disclosed applications.

TECHNICAL FIELD

Provided herein are compounds and methods of using them related to the field of chemistry, biochemistry and medicine. More particularly, disclosed herein are nucleotide, acyclonucleotide and acyclic nucleoside phosphonate (ANP) analogs with the substituted phosphate group, pharmaceutical compositions including one or more of said phosphate substituted nucleotide or ANP analogs, methods of synthesizing the same as well as methods of treating diseases and or conditions using the same.

BACKGROUND

Delivery of active compounds to a patient in need of treatment is typically through systemic delivery of the drug, for example, intravenous delivery or oral delivery. Systemic delivery exposes healthy cells and tissue to the drug, even though the drug is only needed in a certain area of the body. As a result, healthy cells and tissues can be adversely affected by the drug, and higher concentrations of the drug are necessary to deliver appropriate levels to the site needing treatment.

Compositions and methods provided herein address this and other problems in the art.

SUMMARY

Provided herein are compounds, compositions comprising those compounds, methods of making those compounds, and methods of using those compounds.

One aspect relates to compounds of Formula I or pharmaceutically acceptable salts thereof.

Another aspect relates to compounds of Formula II or pharmaceutically acceptable salts thereof.

Yet another aspect relates to compounds of Formula III or pharmaceutically acceptable salts thereof.

Another aspect relates to compounds of Formula IV or pharmaceutically acceptable salts thereof.

Further disclosed herein are methods of synthesis of the compounds of Formulae I-IV.

Still further disclosed herein are methods of delivering nucleotides, acyclonucleotides and ANPs to the inside of the cell by conjugating said compounds with forms and/or moieties of Vitamin $B_6$ (the terms moiety, form, residue, etc. when used with respect to Vitamin $B_6$ are intended to be interchangeable; the vitamin $B_6$ conjugate with nucleotides, acyclonucleotides, or ANPs is referred to as a vitamin $B_6$ derivative of the nucleotides, acyclonucleotides or ANPs).

Also disclosed herein are pharmaceutical compositions comprising one or more compounds of Formula I-IV, one or more pharmaceutically acceptable carriers, diluent excipients or combinations thereof.

Some aspects of the methods disclosed herein relate to treating diseases and/or ameliorating the symptoms of disease, including viral, bacterial, fungal, cancer, inflammatory, or parasitic diseases and treating pain by administering therapeutically effective amounts of one or more compounds of Formulae I-IV or a pharmaceutical composition including the compounds. Such compounds can be used in the manufacture of medicaments used for the treatment of said diseases. Such compounds can be used in treating a variety of diseases.

DETAILED DESCRIPTION

Figure 1:
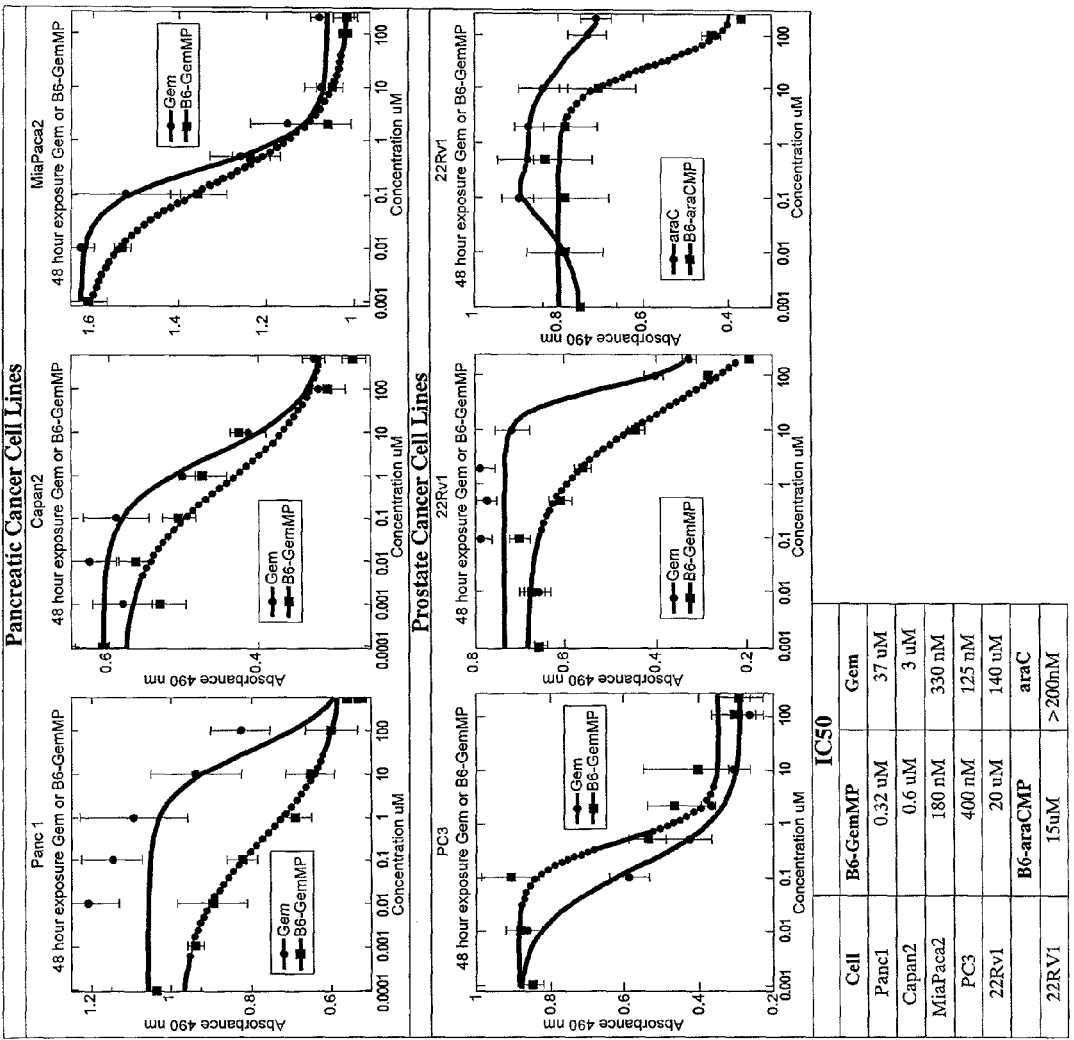
FIG. 1. Antiproliferation of various pancreatic and prostate cancer cells after 48 hours in the presence of Cytarabine or 5'-aracytidilic acid N-pyridoxylamide (compound 3=$B_6$-araCMP) or Gemcitabine or N-pyridoxylamide of 2'-Deoxy-2',2'-difluoro-5'-cytidylic acid (compound 16=$B_6$-GemMP).

Nucleoside analogs represent a class of compounds with broad therapeutic use and biologic activity, for example, antiviral, antibiotic, antifungal, antiparasitic, antitumor, anti-inflammatory, and analgesic activities. Nucleoside analogs are therapeutically inactive compounds that are converted by host or viral enzymes to their active forms, and subsequently inhibit nucleotide-polymerizing enzymes and other nucleotide-dependent enzymes involved in cell or viral metabolism and survival. This activation occurs by metabolic transformation of nucleoside analogs to their respective 5'-mono-, di- and triphosphates. The first step of this process—5'-monophosphorylation—is often rate-limiting.

Disclosed herein are novel vitamin $B_6$ derivatives of nucleotides, acyclonucleotides and ANPs for use in the treatment of, for example, neoplastic, viral, inflammatory, and parasitic diseases. Vitamin $B_6$ uptake into human cells is a carrier-mediated process [Said, H. M., Ortiz, A., and Ma, T. Y. (2003). A carrier-mediated mechanism for pyridoxine uptake by human intestinal epithelial Caco-2 cells: regulation by a PKA-mediated pathway. Am J Physiol Cell Physiol 285, C1219-1225].

It has been determined and disclosed herein that vitamin $B_6$ derivatization of nucleotides and their analogs is well suited for masking negative charge of phosphate group and thus enhance penetration through the cell membrane. However, for those of ordinary skill in the art it is unknown whether the vitamin $B_6$ fragment can be enzymatically or metabolically released when inside the cell in order for the nucleotide analogs to be activated into their 5'-di- and/or triphosphate derivatives to be efficacious.

Unless defined otherwise, all technical and scientific terms used throughout this application have the meanings that are commonly understood by those skilled in the art.

As used herein, an "alkyl" group refers to a saturated aliphatic hydrocarbon, including straight-chain or branched-chain alkyl groups. Preferably, the alkyl group has 1 to 20 carbons. More preferably it is a lower alkyl having from 1 to 10 carbons, and more preferably 1 to 6 carbons. The alkyl group may be substituted or unsubstituted. When substituted, the substituent group(s) may include hydroxy, cyano, alkoxy, $NO_2$ or $N(CH_3)_2$, amino, $N_3$ or SH.

As used herein, "alkenyl" refers to an alkyl group that contains in the straight or branched hydrocarbon chain one or more double bonds. An alkenyl group may be unsubstituted or substituted.

As used herein, "alkynyl" refers to an alkyl group that contains in the straight or branched hydrocarbon chain one or more triple bonds. An alkynyl group may be unsubstituted or substituted.

As used herein, a "cycloalkyl" group refers to a cyclic alkyl group having from three to ten, and preferably five or six carbon atoms forming the alkyl ring.

As used herein, an "aryl" group refers to an aromatic group which has at least one ring having a conjugated pi electron system and includes carbocyclic aryl, heterocyclic aryl and biaryl groups; all of which may be optionally substituted. Substituent(s) on these groups may include halogen, trihalomethyl, hydroxyl, SH, cyano, alkoxy, alkyl, alkenyl, alkynyl, and amino groups.

As used herein, "heteroaryl" refers to an aromatic ring having from 1 to 3 heteroatoms in the aromatic ring with the remainder of the atoms in the ring being carbon atoms. Suitable heteroatoms include oxygen, sulfur, and nitrogen, and exemplary heteraryls include furanyl, thienyl, pyridyl, pyrrolyl, pyrrolo, pyrimidyl, pyrazinyl and imidazolyl. These heteroaryl rings may also be substituted. Substituents on these heteroaryl groups may include halogen, trihalomethyl, hydroxyl, SH, cyano, alkoxy, alkyl, alkenyl, alkynyl, and amino groups.

As used herein, "anti-cancer compound" or "compound having anticancer activity" refers to any compound demonstrating preclinical or clinical anti-cancer activity or is used in clinics for treating patients suffering with cancer.

As used herein, "anti-infective compound" or "compound having anti-infective activity" refers to any compound demonstrating preclinical or clinical anti-viral, anti-bacterial, anti-fungal activity or is used for treating patients suffering from diseases caused by virus, bacteria or fungi respectively.

As used herein, "anti-inflammatory compound" or "compound having anti-inflammatory activity" refers to any compound demonstrating preclinical or clinical anti-inflammatory activity or is used for treating patients suffering from inflammatory diseases.

As used herein, "anti-parasitic compound" or "compound having antiparasitic activity" refers to any compound demonstrating preclinical or clinical anti-parasitic activity or is used for treating patients suffering from parasitic diseases.

As used herein, "analgesic compound" or "compound having analgesic activity" refers to any compound demonstrating preclinical or clinical reduction or elimination of pain or is used for treating patients suffering from pain.

As used herein, an "unmodified nucleic (or heterocyclic) base" or "natural nucleic base" is any base found in a nucleic acid including adenine, cytosine, guanine, uracil, and thymine having no additional substituents or modifications.

As used herein, a "modified nucleic (or heterocyclic) base" is any base found in a nucleic acid which contains any modification in the chemical structure relative to an unmodified nucleic base.

As used herein, an "unmodified sugar" is beta-D-ribofuranose or 2-deoxy-beta-D-ribofuranose.

As used herein, a "modified sugar" is any sugar moiety containing any modification in the chemical structure of an unmodified sugar.

A 5'-nucleoside or acyclonucleoside is attached to the chemical structures provided herein as a residue or moiety of a 5'-nucleoside or acyclonucleoside (in other words, a 5'-nucleosidyl or acyclonucleosidyl residue). The terms 5'-nucleoside and 5'-nucleosidyl, as well as acyclonucleoside and acyclonucleosidyl, are used interchangeably throughout the specification, though it is understood that one of skill in the art would understand that it is the residue that attaches to provide the chemical structures disclosed herein. Such residues include, for example, $O^-$, $CH_2^-$, etc.

It is understood that, in any compound described herein having one or more chiral centers, if an absolute stereochemistry is not expressly indicated, then each center may independently be of R-configuration or S-configuration or a mixture thereof. Hence, the compounds provided herein may be enantiomerically pure or be stereoisomeric mixtures. It is also understood that, in any compound described herein having one or more double bond(s) generating geometrical isomers that can be defined as E or Z, each double bond may independently be E or Z or a mixture thereof. Likewise, all tautomeric forms are also intended to be included.

In some embodiments, compounds disclosed herein have the chemical structure I:

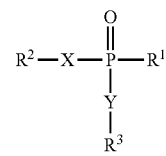

wherein $R^1$ is a 5'-nucleosidyl or acyclonucleosidyl residue or analog thereof, having anticancer, antiviral, anti-inflammatory, antiinfective, analgesic, or antiparasitic activity;

X and Y are independently O, S, or N;

$R^2$ and $R^3$ are independently chosen from the group consisting of H, phenyl, alkyl, aryl, and heteroaryl, and vitamin $B_6$ forms/moieties having any one of the following structures:

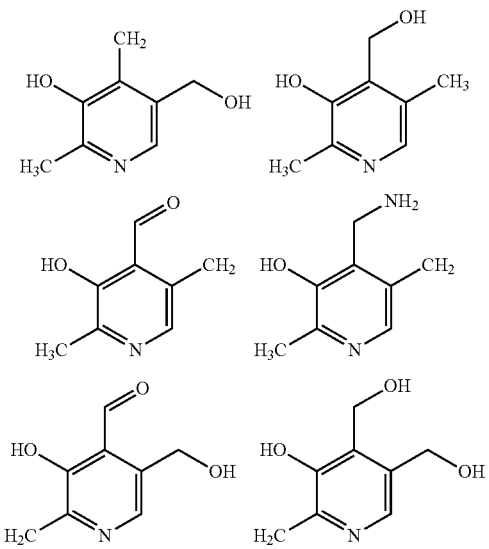

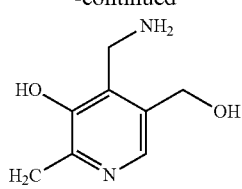

wherein at least one of $R^2$ and $R^3$ is a vitamin $B_6$ moiety. The vitamin $B_6$ moiety attaches to the X or Y at the $CH_2$.

Exemplary $R^1$ compounds include but are not limited to cytarabine, fludarabine, gemcitabine, clofarabine, cladribine, vidaza, dacogen, pentostatin, aristeromycin, acyclovir, gancyclovir, pencyclovir, adefovir, cidofovir, tenofovir, zidovudine, lamivudine, and cladribine.

Examples of 5'-nucleosides and their analogs include but are not limited to the following:

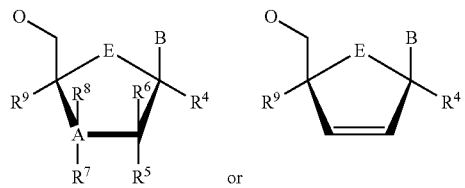

wherein B is modified or unmodified nucleic base;

E is O, C, N, or S;

A is C, S, or O; and $R^4$, $R^5$, $R^6$, $R^7$, $R^8$ and $R^9$ are independently, H, OH, F, $NH_2$, $N_3$, alkyl, alkenyl, or alkynyl.

Examples of the acyclonucleosides include but are not limited to:

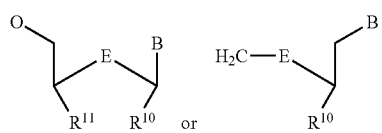

wherein B is a modified or unmodified nucleic base;

E is O or C; and $R^{10}$ and $R^{11}$ are independently H, OH, F, $NH_2$, $N_3$, alkyl, alkenyl, or alkynyl.

Another embodiment relates to the compounds having chemical structure II:

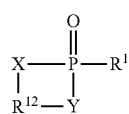

wherein $R^1$ is a 5'-nucleosidyl or acyclonucleosidyl residue or analog thereof having anticancer, antiviral, anti-inflammatory, antiinfective, analgesic, or antiparasitic activity;

X and Y are independently O, S, or N;

$R^{12}$ is the vitamin $B_6$ moiety having structure:

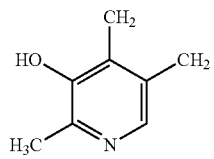

wherein the vitamin $B_6$ moiety attaches to the X and Y at the $CH_2$ molecules on the $B_6$ moiety.

Exemplary $R^1$ compounds include but are not limited to cytarabine, fludarabine, gemcitabine, clofarabine, cladribine, vidaza, dacogen, pentostatin, aristeromycin, acyclovir, gancyclovir, pencyclovir, adefovir, cidofovir, tenofovir, zidovudine, lamivudine, and cladribine.

Examples of 5'-nucleosides and their analogs include but are not limited to the following:

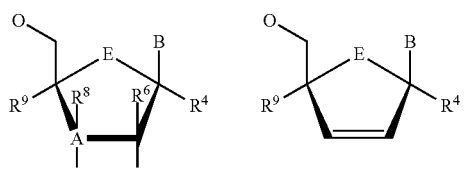

wherein B is a modified or unmodified nucleic base;

E is O, C, N, or S;

A is C, S, or O; and $R^4$, $R^5$, $R^6$, $R^7$, $R^8$ and $R^9$ are independently selected from the group consisting of H, OH, F, $NH_2$, $N_3$, alkyl, alkenyl, and alkynyl.

Examples of the acyclonucleosides include but are not limited to:

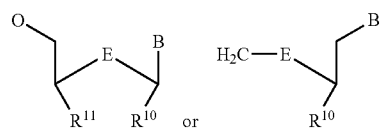

wherein B is a modified or unmodified nucleic base;

E is O or C; and $R^{10}$ and $R^{11}$ are independently selected from the group consisting of H, OH, F, $NH_2$, $N_3$, alkyl, alkenyl, and alkynyl.

Another embodiment relates to the compounds having chemical structure III:

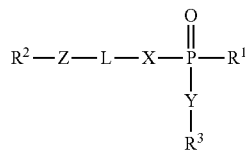

wherein R¹ is a 5'-nucleosidyl or acyclonucleosidyl residue having anticancer, antiviral, anti-inflammatory, antiinfective, analgesic, or antiparasitic activity;

X, Y and Z are independently O, S, or N;

R² and R³ are independently chosen from the group consisting of H, phenyl, alkyl, aryl, heteroaryl, and vitamin B₆ moieties having the structure

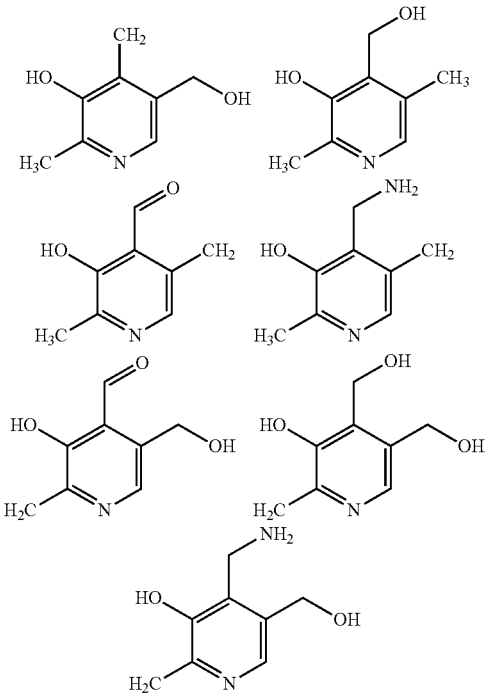

wherein at least one of R² and R³ is a vitamin B₆ moiety. The vitamin B₆ moiety attaches to the Z or Y at the CH₂; and L is alkyl, alkenyl or alkynyl.

Exemplary R¹ compounds include but are not limited to cytarabine, fludarabine, gemcitabine, clofarabine, cladribine, vidaza, dacogen, pentostatin, aristeromycin, acyclovir, gancyclovir, pencyclovir, adefovir, cidofovir, tenofovir, zidovudine, lamivudine, and cladribine.

Examples of 5'-nucleosides and their analogs include but are not limited to the following:

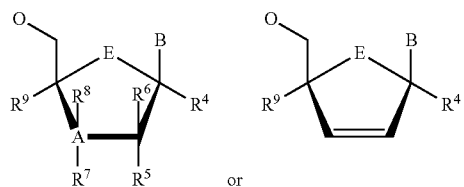

wherein B is a modified or unmodified nucleic base;

E is O, C, N, or S;

A is C, S, or O;

R⁴, R⁵, R⁶, R⁷, R⁸ and R⁹ are independently selected from the group consisting of H, OH, F, NH₂, N₃, alkyl, alkenyl, and alkynyl.

Examples of the acyclonucleosides include but are not limited to:

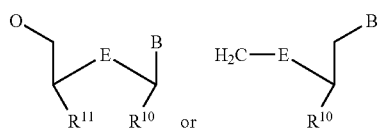

wherein B is a modified or unmodified nucleic base;

E is O or C;

R¹⁰ and R¹¹ are independently selected from the group consisting of H, OH, F, NH₂, N₃, alkyl, alkenyl, and alkynyl.

Another embodiment relates to the compounds having chemical structure IV:

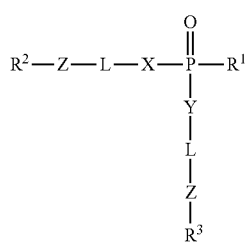

wherein R¹ is a 5'-nucleosidyl or acyclonucleosidyl residue having anticancer, antiviral, anti-inflammatory, antiinfective, analgesic, or antiparasitic activity;

X, Y and Z are independently O, S, or N;

R² and R³ are independently chosen from the group consisting of H, phenyl, alkyl, aryl, heteroaryl, and vitamin B₆ moieties having the structure

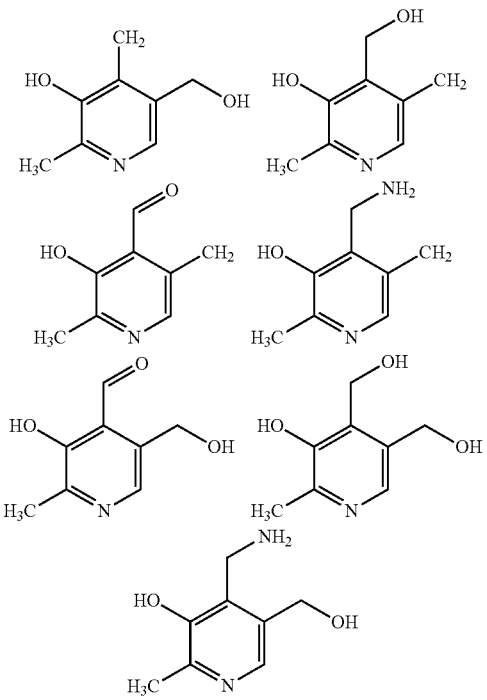

wherein at least one of $R^2$ and $R^3$ is a vitamin $B_6$ moiety. The vitamin $B_6$ moiety attaches to the Z or Y at the $CH_2$; and L is alkyl, alkenyl or alkynyl.

Exemplary $R^1$ compounds include but are not limited to cytarabine, fludarabine, gemcitabine, clofarabine, cladribine, vidaza, dacogen, pentostatin, aristeromycin, acyclovir, gancyclovir, pencyclovir, adefovir, cidofovir, tenofovir, zidovudine, lamivudine, and cladribine.

Examples of 5'-nucleosides and their analogs include but are not limited to the following:

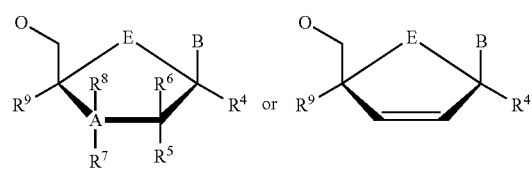

wherein B is a modified or unmodified nucleic base;

E is O, C, N, or S;

A is C, S, or O;

$R^4$, $R^5$, $R^6$, $R^7$, $R^8$ and $R^9$ are independently selected from the group consisting of H, OH, F, $NH_2$, $N_3$, alkyl, alkenyl, and alkynyl.

Examples of the acyclonucleosides include but are not limited to:

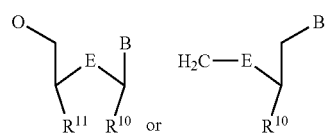

wherein B is a modified or unmodified nucleic base;

E is O or C;

$R^{10}$ and $R^{11}$ are independently selected from the group consisting of H, OH, F, $NH_2$, $N_3$, alkyl, alkenyl, and alkynyl.

TABLE 1

Exemplary nucleosides

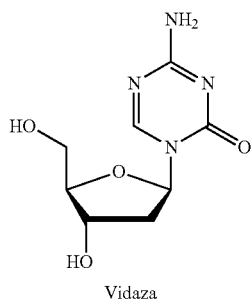

Vidaza

TABLE 1-continued

Exemplary nucleosides

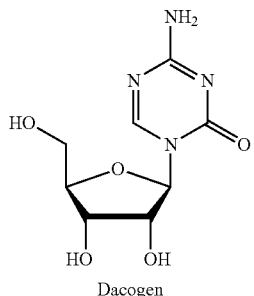

Dacogen

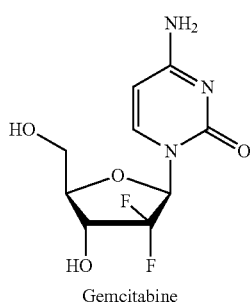

Gemcitabine

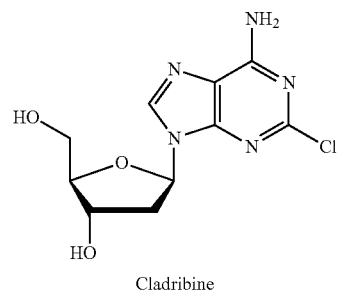

Cladribine

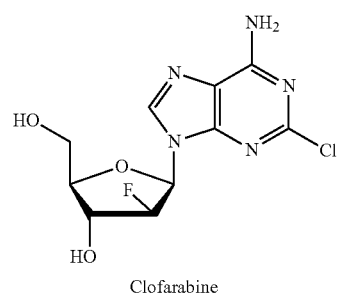

Clofarabine

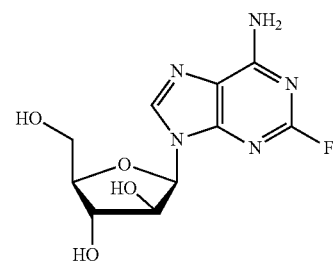

Fludarabine

TABLE 1-continued

Exemplary nucleosides

Pentostatin

Zidovudine

Lamivudine

Cytarabine

TABLE 2

Exemplary acyclonucleosides

Acyclovir

TABLE 2-continued

Exemplary acyclonucleosides

Gancyclovir

Pencyclovir

Adefovir

Cidofovir

Tenofovir

The exemplary nucleosides and acyclonucleosides shown in Tables 1 and 2 would attach as $R^1$ in their 5'-nucleosidyl or acyclonucleosidyl residue or analog forms, e.g. would attach through the 5'-O⁻ (compounds in Table 1), through any of the O⁻ in the acyclo part (compounds in the first row of Table 2) or through the $CH_2^-$ of the phosphonate part (compounds in second row of Table 2).

Also contemplated herein are the pharmaceutically acceptable non-toxic acid addition salts of the compounds described herein and pharmaceutically acceptable formulations containing them. Such salts include those derived from organic and inorganic acids such as, without limitation, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embonic acid, enanthic acid, and the like.

The pharmaceutical compositions described herein are preferably formulated in unit dosage form, meaning physically discrete units suitable as a unitary dosage, or a predetermined fraction of a unitary dose to be administered in a single or multiple dosage regimen to human subjects and other mammals, each unit containing a predetermined quantity of active material calculated to produce the desired therapeutic effect in association with a suitable pharmaceutical excipient or excipients. The compositions can be formulated so as to provide sustained or delayed release of active ingredient after administration to the patient by employing procedures well known in the art.

Pharmaceutical compositions provided herein comprise one or more compounds of formulae I-IV associated with at least one pharmaceutically acceptable carrier, diluent or excipient. In preparing such compositions, the active ingredients are usually mixed with or diluted by an excipient or enclosed within such a carrier, which can be in the form of a capsule or sachet. When the excipient serves as a diluent, it may be a solid, semi-solid, or liquid material, which acts as a vehicle, carrier, or medium for the active ingredient. Thus, the compositions can be in the form of tablets, pills, powders, elixirs, suspensions, emulsions, solutions, syrups, soft and hard gelatin capsules, suppositories, sterile injectable solutions and sterile packaged powders.

Examples of suitable excipients include lactose, dextrose, sucrose, sorbitol, mannitol, starch, gum acacia, calcium silicate, calcium phosphate, alginates, tragacanth, gelatin, microcrystalline cellulose, polyvinylpyrrolidinone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

In preparing a pharmaceutical formulation comprising one or more compounds described herein, it may be necessary to mill the active compound to provide the appropriate particle size prior to combining with the other ingredients. If the active compound is substantially insoluble, it is ordinarily milled to a particle size of less than 200 mesh. If the active compound is substantially water soluble, the particle size is normally adjusted by milling to provide a substantially uniform distribution in the formulation, e.g. about 40 mesh.

The tablets or pills comprising compounds provided herein may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer, which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the oral or nasal respiratory route for local or systemic effect administers the compositions. Compositions in pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, preferably orally or nasally, from devices, which deliver the formulation in an appropriate manner.

Another embodiment provided herein relates to the method of delivering nucleotides, acyclonucleotides and ANPs inside the cell by masking charged phosphate group of the said compounds with different forms of vitamin $B_6$ (i.e. different moieties, different residues) and/or by using cell uptake mechanisms not available to nucleotides, acyclonucleotides and ANPs. The uptake mechanisms include but are not limited to facilitated transporters of vitamin $B_6$ and would be a function of the vitamin $B_6$ moiety enabling passage of the nucleotides through the cell membrane. Preferably the resulting conjugates or pro-drugs have the general structures disclosed in Formulae I-IV.

Another embodiment provided herein is a novel compound of Formulae I-IV or a pharmaceutical composition comprising a novel compound of Formulae I-IV for use in ameliorating or treatment of neoplastic diseases, infectious diseases caused by viral, bacterial or fungal infections or parasitic diseases.

Another embodiment provided herein is a novel compound of Formulae I-IV or a pharmaceutical composition comprising a novel compound of Formulae I-IV for use in ameliorating or treatment of pain.

As used herein, the terms "ameliorating" or "ameliorate" indicate an improvement or bettering of a disease, an infection, a condition, or pain, e.g. to make more tolerable.

As used herein, the terms "treat" or "treatment" refer to both therapeutic treatment and prophylactic, maintenance, or preventative measures, wherein the object is to prevent an undesired physiological condition, or obtain beneficial or desired clinical results including a reduction in the severity of symptoms or diminishing the underlying causes of the symptoms. Treatment includes eliciting a clinically significant response, without excessive levels of side effects.

Neoplastic diseases include but not limited to cancer and leukemia. Viral diseases include but are not limited to those caused by a virus selected from the group consisting of an adenovirus, an Alphaviridae, an Arbovirus, an Astrovirus, a Bunyaviridae, a Coronaviridae, a Filoviridae, a Flaviviridae, a Hepadnaviridae, a Herpesviridae, an Alphaherpesvirinae, a Betaherpesvirinae, a Gammaherpesvirinae, a Norwalk Virus, an Astroviridae, a Caliciviridae, an Orthomyxoviridae, a Paramyxoviridae, a Paramyxoviruses, a Rubulavirus, a Morbillivirus, a Papovaviridae, a Parvoviridae, a Picornaviridae, an Aphthoviridae, a Cardioviridae, an Enteroviridae, a Coxsackie virus, a Polio Virus, a Rhinoviridae, a Phycodnaviridae, a Poxviridae, a Reoviridae, a Rotavirus, a Retroviridae, an A-Type Retrovirus, an Immunodeficiency Virus, a Leukemia Viruses, an Avian Sarcoma Viruses, a Rhabdoviruses, a Rubiviridae and a Togaviridae. Inflammatory diseases include but are not limited to Multiple Sclerosis. Parasitic diseases include but are not limited to Chaga's disease.

Other embodiments provided herein are novel compounds of Formulae I-IV or their pharmaceutical compositions for use in ameliorating or treatment of pain.

In other embodiments, any of the compounds according to Formulae I-IV or their pharmaceutical compositions can be used as a medicament.

In further embodiments, any of the compounds according to Formulae I-IV or their pharmaceutical compositions can be used in the therapy of a disease caused by a bacterial infection, a fungal infection, a viral disease, a neoplastic disease, an inflammatory disease, a parasitic disease, or pain.

In still further embodiments, any of the compounds according to Formulae I-IV or their pharmaceutical compositions can be used for the manufacture of a medicament for the treatment of a disease caused by a bacterial infection, a fungal infection, a viral disease, a neoplastic disease, an inflammatory disease, a parasitic disease, or pain.

Another embodiment provided herein is a method of delivering nucleoside- or acyclonucleoside-monophosphates or ANPs into a cell using the compounds of Formulae I-IV or the pharmaceutical compositions comprising such compounds. This method can be performed in vitro or in vivo.

Additional objects, advantages, and novel features of this invention will become apparent to those skilled in the art upon examination of the following examples thereof, which are not intended to be limiting.

Various publications are cited herein, the disclosures of which are incorporated by reference in their entireties. Such publications can provide exemplary, procedural or other details supplementary to those set forth herein. Nothing herein is to be construed as an admission that the present disclosure is not entitled to antedate such publication by virtue of prior invention. Further, the dates of publication provided may be different from the actual publication dates which may need to be independently confirmed.

While embodiments of the invention have been shown and described, modifications thereof can be made by one skilled in the art without departing from the spirit and teachings of the disclosure. The embodiments described herein are exemplary only, and are not intended to be limiting. Many variations and modifications of the compounds and methods disclosed herein are possible and are within the scope of the invention. Where numerical ranges or limitations are expressly stated, such express ranges or limitations should be understood to include iterative ranges or limitations of like magnitude falling within the expressly stated ranges or limitations. Use of broader terms such as comprises, includes, having, etc. should be understood to provide support for narrower terms such as consisting of, consisting essentially of, comprised substantially of, and the like. Accordingly, the scope of protection is not limited by the description set out above but is only limited by the claims which follow, that scope including all equivalents of the subject matter of the claims. Each and every original claim is incorporated into the specification as an embodiment of the invention. Thus, the claims are a further description and are an addition to the preferred embodiments disclosed herein.

Examples 1. 5'-aracytidilic acid N-pyridoxylamide

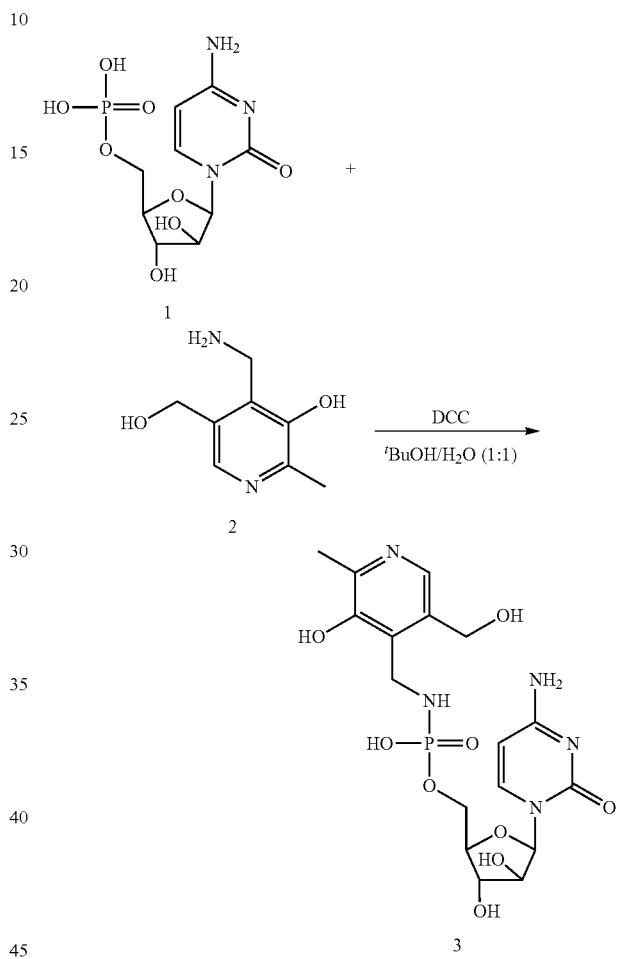

To a solution of 2.02 g of $NaHCO_3$ in 20 mL of water was added 2.41 g of pyridoxamine dihydrochloride with stirring. The resultant clear solution on standing overnight deposited a crystalline precipitate. The precipitate was collected by filtration, washed with water and dried.

To a solution of 1-β-D-arabinofuranosylcytosine 5'-monophosphate 1 (230 mg, 0.71 mmol) in $H_2O/^tBuOH$ (1:1; 15 ml), pyridoxamine 2 (480 mg, 2.85 mmol, 4 equiv.) was added and the reaction mixture was heated to reflux. A solution of dicyclohexylcarbodiimide (588 mg, 2.85 mmol, 4 equiv.) in $^tBuOH$ (11.4 ml, 0.25M) was slowly added and refluxed overnight. The reaction mixture was cooled to room temperature and the solids formed were filtered. Evaporation of the solvents followed by purification by flash column chromatography ($CH_2Cl_2$/MeOH 9:1 to 1:1) afforded the desired product 3 (85 mg, 0.179 mmol, 25% yield).

$^1$H NMR (500 MHz, DMSO/$D_2O$ exchange): δ 7.7 (s, 1H), 7.67 (d, J=7.5 Hz, 1H), 6.03 (d, J=4 Hz, 1H), 5.78 (d, J=7 Hz, 1H), 4.47 (s, 2H), 3.99 (m, 3H), 3.93 (m, 1H), (3.86-3.80 (m, 3H), 2.8 (s, 3H).

Removal of pyridoxamine-N,N'-dicyclohexylcarboxami-dinium counter ion

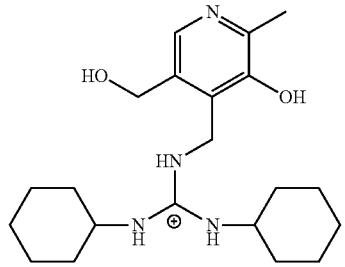

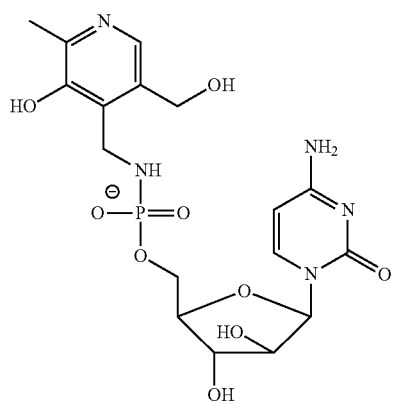

In the above reaction conditions when H$_2$O/$^t$BuOH in the ratio of 1:5 was used, the product was obtained as the carboxamidinium salt 4. The counter ion was removed to obtain as a free acid is as follows. A glass column was loaded with 5 ml of Dowex 50WX8 (H+ form) and thoroughly washed with DI water (5 CV). 0.2 mmol of carboxamidinium salt was loaded on the column and the column was washed further with water (2 CV). Finally the product was eluted with 2.5% NH$_4$OH solution. The appropriate fractions were evaporated and the product was dried under high vacuum to afford the desired product 3.

2. N-pyridoxyl-Lysine-Fmoc (5)

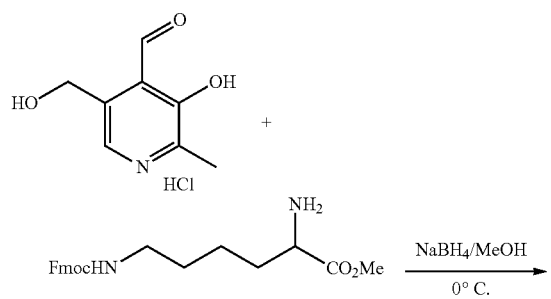

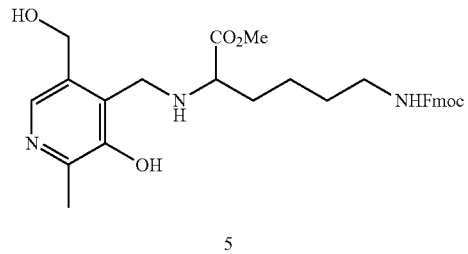

5

To a stirred cold solution of H-Lys(Fmoc)-OMe HCl (1.047 g, 2.5 mmol) in MeOH (10 ml) was added KOH (0.2 g) and pyridoxal hydrochloride (560 mg, 2.75 mmol). The resultant mixture was stirred for 1 h and then NaBH$_4$ (133 mg, 3.5 mmol) was added slowly at 0° C. The mixture was further stirred for 1 h at room temperature and then water was added. The crude mixture was extracted with CH$_2$Cl$_2$, washed with brine, dried (Na$_2$SO$_4$) and evaporated under vacuo. Purification by flash column chromatography (CH$_2$Cl$_2$/MeOH 9:1) provided the desired compound 5 (300 mg, 30% yield).

$^1$H NMR (500 MHz, CDCl$_3$): δ 7.89 (s, 1H), 7.78 (d, J=5 Hz, 2H), 7.60 (d, J=5 Hz, 2H), 7.41 (m, 2H), 7.32 (m, 2H), 4.90 (s, 1H), 4.60 (m, 2H), 4.43 (d, J=5 Hz, 2H), 4.22 (m, 1H), 4.10 (dd, J=15, 80 Hz, 2H), 3.79 (s, 3H), 3.34 (m, 1H), 3.20 (d, J=5 Hz, 1H), 2.48 (s, 3H), 1.76 (m, 2H), 1.53 (m, 2H), 1.28 (m, 2H).

3. Removal of Fmoc Protection

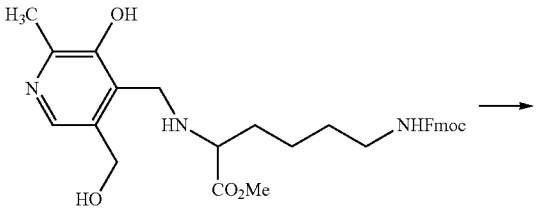

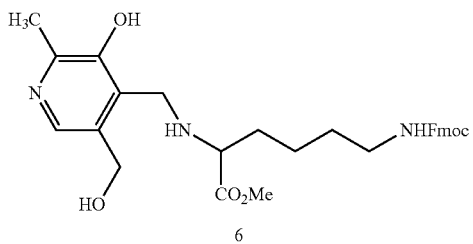

6

Fmoc protected compound 5 (200 mg, 0.374 mmol) was added to piperidine (0.074 ml, 0.748 mmol) in DMF (0.3 ml) at RT. The resulting mixture was stirred at room temperature for 2 h and then the solvents were evaporated. The crude product 6 was used in the next step without further purification.
4. Conjugate of pyridoxyllysine and arabinocytidine-5'-phosphate (7)
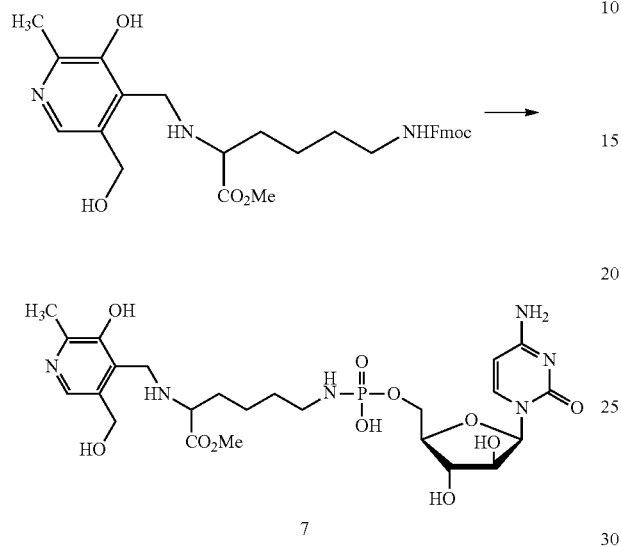
7
Compound 7 was prepared analogously to compound 3.
5. N-pyridoxylamide of 2'-Deoxy-2',2'-difluoro-5'-cytidylic acid 6 $B_6$-GemMP)
The title compound was prepared according to the scheme below.
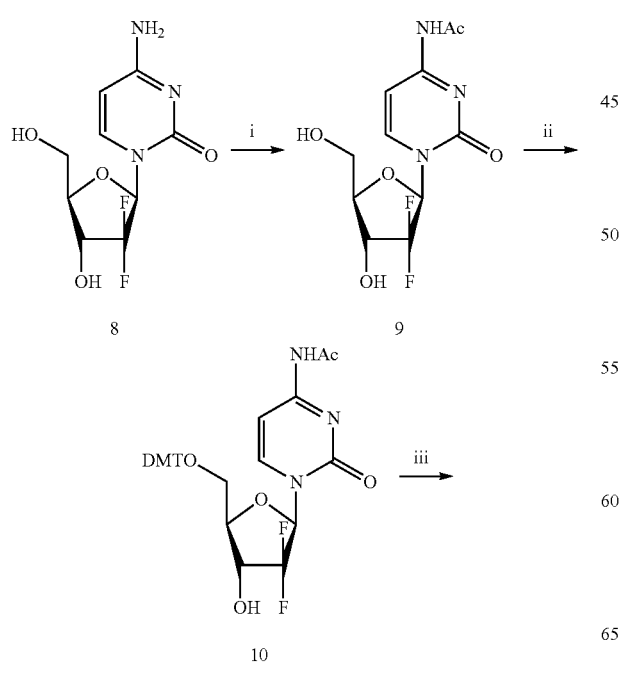
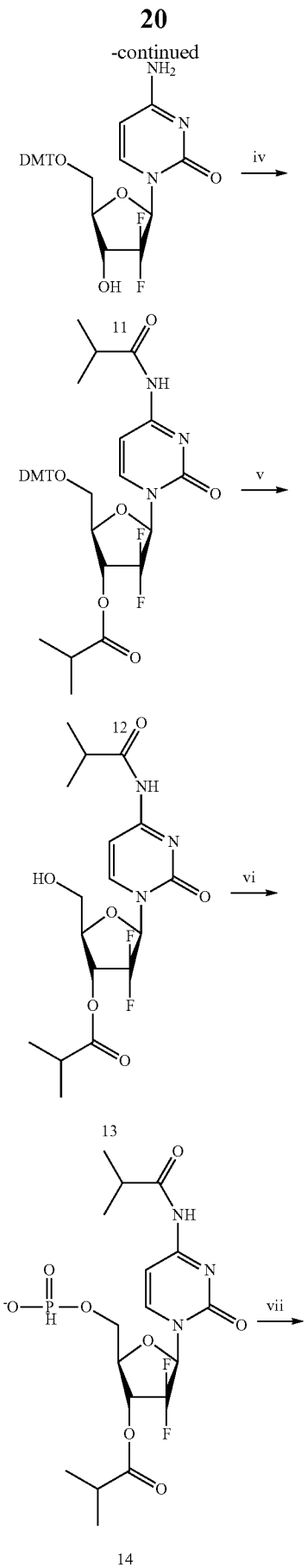

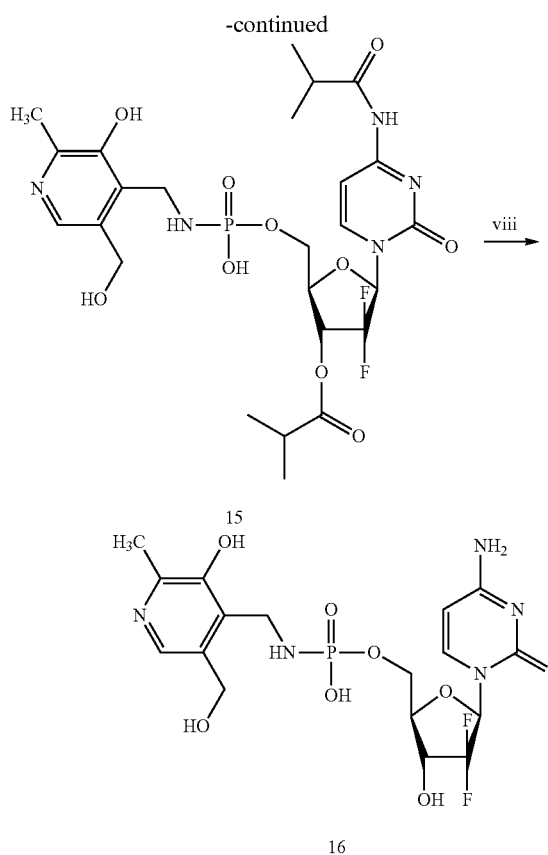

Reagents & Conditions:

i) Ac₂O/MeOH; ii) DMTCl/Py; iii) NH₄OH; iv) iPrCOCl/Py; v) Cl₂CHCOOH/DCM/MeOH; vi) (PhO)₂P(O)H/Py/MeCN; vii) TMSCl/Py, then I₂, then 2 (pyridoxamine)/TM-SCl/Et₃N; water; viii) NH₄OH 2'-Deoxy-2',2'-difluorocytidine 8 was purchased from Carbosynth Ltd. N-Acetyl derivative 9 was prepared analogously to [Ludwig, Peter S.; Schwendener, Reto A.; Schott, Herbert. Synthesis, 2002(16), 2387-2392]: a mixture of 8 (6.94 g), Ac₂O (4.03 mL), water (15.5 mL), and dioxane (126 mL) was heated at 70° C. for 2 h 20 min, concentrated in vacuo, and mixed with acetonitrile. Precipitate was filtered off, washed with acetonitrile, and dried in vacuo at 60° C. for 18 h to give 6.30 g of compound 9. Concentration of filtrate and dilution it with acetonitrile was repeated two more times to give 0.608 g, and 0.112 g of 9. Combined yield 7.02 g.

To the solution of compound 9 (7.02 g) in pyridine (37 g) DMTCl (8.18 g, 1.05 eq.) was added at 0° C., and the reaction mixture was stirred at room temperature overnight, concentrated in vacuo at 50° C., distributed between ethylacetate and 5% aqueous NaHCO₃. Organic phase was dried over Na₂SO₄, concentrated in vacuo, and purified on silica gel column using a gradient from 50% hexanes in DCM, to 5% MeOH in DCM. Yield 11.01 g (70.6%) of pure 10. Compound 10 (11.01 g) was heated in a sealed tube with pyridine (33 mL) and concentrated aqueous ammonia (8 g) at 50° C. for 3 h, concentrated in vacuo, distributed between ethylacetate and 5% aqueous NaHCO₃. Organic phase was separated, dried over Na₂SO₄, and concentrated in vacuo to give pure compound 11 in quantitative yield.

Compound 11 (2.6 g, 4.28 mmol) was dissolved in a mixture of pyridine (2.5 mL), and acetonitrile (2.5 mL), and treated with iPrCOCl (0.994 mL, 1.1 eq.) of at 0-25° C. until bis-acylation was complete according to TLC analysis (5% MeOH in DCM) (approximately 2 h). Reaction mixture was distributed between ethylacetate and 5% aqueous NaHCO₃, organic phase was separated, dried over Na₂SO₄, and concentrated in vacuo to give compound 12 as a white solid foam (3.00 g), which was used without further purification.

To remove DMT protective group, compound 12 (3.00 g) was treated with 10% solution of MeOH in DCM (40 mL) containing Cl₂HCCOOH (3% v/v) until the deprotection of compound 12 was complete (6 h at room temperature, and overnight at 0° C.).

The reaction mixture was neutralized with 5% aqueous NaHCO₃ and extracted with DCM. Organic phase was separated, dried over Na₂SO₄, concentrated in vacuo, and purified on silica gel using a gradient of MeOH (0-4%) in DCM, providing compound 13 in 68% yield.

Compound 13 (1.17 g) was treated with (PhO)₂P(O)H (1.66 mL, 3 eq) in pyridine at 0-25° C. for 2 h. Reaction mixture was concentrated in vacuo, then co-evaporated 3 times with toluene, 2 times with acetonitrile, 2 times with DCM, and, finally, co-evaporated with 5 g of silica gel, and DCM to obtain a sample pre-loaded into silica gel. This material was applied to the starting zone of a flash column and eluted with a gradient from 2% TEA, 48% hexanes in DCM to 2% TEA, 4% MeOH in DCM. After drying in vacuo over P₂O₅, a TLC-pure 14 was obtained in a yield of 2.09 g. However, 31P NMR spectrum showed ~25% contamination of compound 14 with PhOPO₂H. This mixture was used as is on the next step.

Compound 14 (1.83 g) was dissolved in pyridine (6.5 mL) and treated with Me₃SiCl (1.2 mL) for 0.5 h at 0-25° C. under vigorous stirring to give a suspension of a white solid. Concentrated solution of iodine in THF was then added dropwise at 0° C. over a period of ~1 min under vigorous stirring. First drops of iodine decolorized instantly, however the final solution was brownish. After another 2 min of stirring, the reaction mixture was treated with a mixture consisting of pyridoxamine free base (0.793 g), Me₃SiCl (0.75 mL), TEA (2.1 mL), and pyridine (prepared in advance by stirring for 0.5 h at room temperature before use). After 0.5 h, combined reaction mixture was concentrated in vacuo and purified on silica gel (DCM→DCM, 15% MeOH, 2% TEA) to provide amidate 15 in a yield of 0.189 g.

Compound 15 (0.189 g) was treated with a mixture of conc. aq ammonia and methanol (1:2 v/v) at room temperature for 48 h. Reaction mixture was concentrated in vacuo and purified on silica gel (iPrOH, 4% NH₄OH iPrOH, 4% NH₄OH, 40% MeOH) to give 0.134 g of compound 16 as a solvate with iPrOH. To remove isopropanol, compound 16 was repeatedly lyophilized from aqueous solution until no iPr group was detectable in 1H NMR spectrum (5 times). Final yield 0.054 g.

6. Antiproliferative Activity of 3 and 16, Stability in Growth Media and in Vivo Activity Summary The N-pyridoxylamide of 5'-aracytidilic acid (B₆-araCMP, compound 3) and the N-pyridoxylamide of 2'-Deoxy-2',2'-difluoro-5'-cytidylic acid (B₆-GemMP) were prepared, shown to be stable in buffers and media over the time course of experiments, demonstrated accelerated uptake by cells, improved anti-proliferative activity and inhibited tumor progression in vivo. Preliminary cell based data was generated in three pancreatic cell lines (Capan2, Panc1 and MiaPaca), two prostate cancer cell lines (PC3 and 22Rv1), and rodent multiple myeloma cell line 5TGM1; in vivo data was generated in immunocompromised mice with subcutaneous implants of Capan2 cells.

Methods and Data

Potent Antiproliferation Observed (Prostate and Pancreatic Cancer Cell Lines):

In a 96-well plate, each well was prepared to contain 50 uL of 50,000 cells in media (HyClone IMDM Modified+4 mM L-Glu, HEPES with 10% Fetal Bovine Serum) to which was added 50 uL media containing either the free nucleoside (cytarabine or gemcitabine) or the conjugate (compound 3 or 16) that achieved the following final concentrations: 0, 0.1, 0.2, 0.5, 1, 3, 10, or 100 uM. The cells were incubated at 37° C. with 5% $CO_2$ for 24, 48 or 72 hours (data trends similarly for all incubation periods while the 48 hour data is shown). The Promega MTS based proliferation assay kit (Promega; CellTiter 96® $AQ_{ueous}$ Non-Radioactive Cell Proliferation Assay (MTS)) was used as per manufacturer's instructions. In short, to each well 100 uL of MTS/PMS reagent was added and allowed to incubate for approximately 2 hours at 37° C. to achieve a colorimetric indication of active cell metabolism. This was quantitated by reading the visible absorption at 415 nm. The data (FIG. 1) was normalized to the absorption range defined from minimal absorbance (media absent cells and drug present), to maximum absorbance (media with cells in the absence of drug). All points were measured in triplicate and averaged before normalization to a 0-100% range. Data was plotted (FIG. 1) as percent inhibition versus log of the compound concentration. Where sigmodial curve fitting was possible, a four-parameter logistic non-linear regression model equation was used to generate the curves and $IC_{50}$ values. As FIG. 1 and the table insert illustrates, the pyridoxamine conjugates frequently demonstrate significantly improved potency in a number of cell lines. The pulse chase experiments shown in FIG. 2 were done as described above with the one alteration that at either the 10 or 60 time point after addition of drug the media was replaced with drug-free media and the cells were allowed to continue incubation for a total of 48 hours. In FIG. 2, the left graph shows the results of 10 or 60 minutes of exposure to Gem or $B_6$-GemMP in 22Rv1 cells with 48 hours post incubation in fresh media prior to MTS assay. Data points were collected in quintuplicate; error bars show standard deviations. The right graph shows the results of a 60 minute pulse of the compounds over a range of concentrations in Capan2 cells. Sigmodial curve fitting employed a four-parameter logistic non-linear regression model equation.

Figure 3:
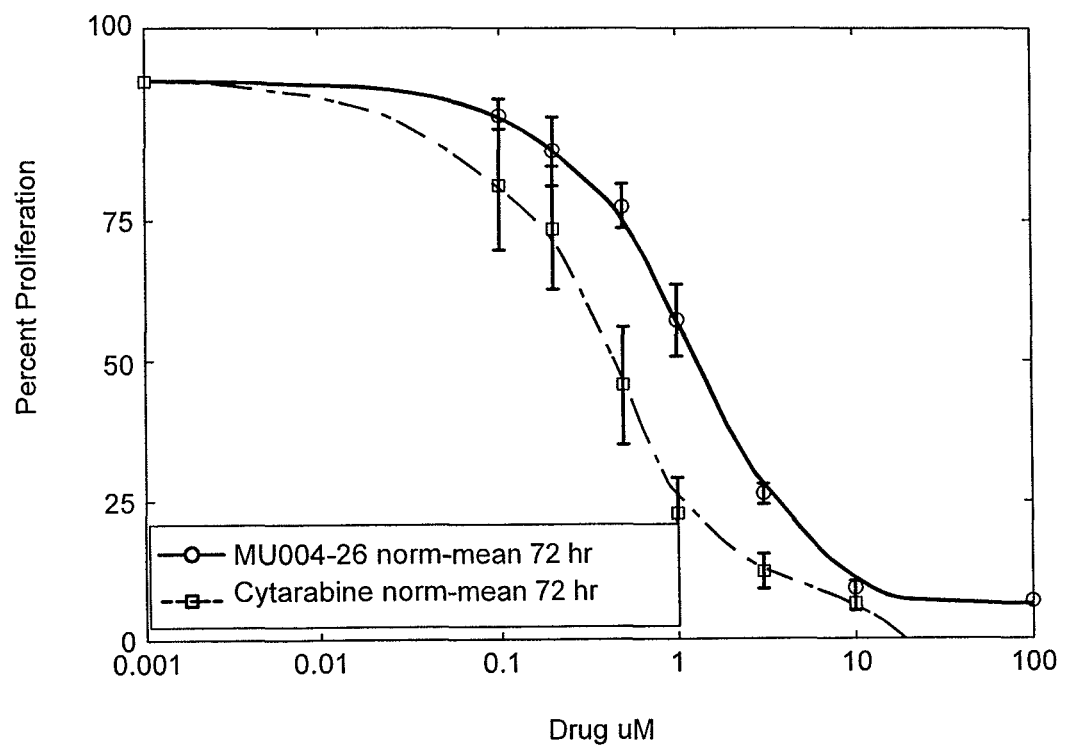
FIG. 3. Antiproliferation of multiple myeloma cancer cells after 72 hours in the presence of Cytarabine or 5'-aracytidilic acid N-pyridoxylamide (compound 3=MU004-26=$B_6$-araCMP).

Potent Antiproliferation Observed (Rodent Multiple Myeloma Cell Line):

In a 96-well plate, each well was prepared to contain 50 uL of 50,000 5TGM1 cells in media (HyClone IMDM Modified+4 mM L-Glu, HEPES with 10% Fetal Bovine Serum) to which was added 50 uL media containing cytarabine or compound 3 (MU004-26) that achieved the following final concentrations: 0, 0.1, 0.2, 0.5, 1, 3, 10, or 100 uM. The cells were incubated at 37° C. with 5% $CO_2$ for 24, 48 or 72 hours (data trends similarly for all incubation periods while the 72 hour data is shown). The Promega TMS based proliferation assay kit was used as per manufacturer's instructions. In short, to each well 100 uL of MTS/PMS reagent was added and allowed to incubate for approximately 2 hours at 37° C. to achieve a colorimetric indication of active cell metabolism. This was quantitated by reading the visible absorption at 415 nm. The data (FIG. 3) was normalized to the absorption range defined from minimal absorbance—media absent cells and drug present, to maximum absorbance—media with cells in the absence of drug. All points were measured in triplicate and averaged before normalization to a 0-100% range. Data was plotted (FIG. 3) as percent inhibition versus log of the compound concentration. As the FIG. 3 illustrates the Cytarabine $IC_{50}$=0.5 uM while the Conjugate $IC_{50}$=1 uM.

Conjugate Stability in Media Observed:

The rapid release of nucleoside or nucleotide from the conjugate into the growth media appeared to be ruled out. To test for this event conjugate 3 was incubated in isotonic saline, sterile media or media that was conditioned by 3 days of cell growth. In conditioned media the cells were removed from the media by centrifugation and conjugate was added to the media and incubated at 37° C. for 0.25, 24 and 72 hours. Proteins and large molecules were removed via precipitation with a 5:4:1 v:v:v mixture of Acetonitrile:methanol:1% Formic acid and subsequent centrifugation. The supernatant (100 uL injection volume) was subjected to HPLC analysis on DNA Pac PA 200 (Dionex, USA) column in a gradient of 400 mM ammonium acetate in 20% acetonitrile (3-40% over 10 minutes). At the three incubation times tested neither free cytarabine nor free pyridoxamine (or any other pyridoxyl based compound) was detected.

Figure 2:
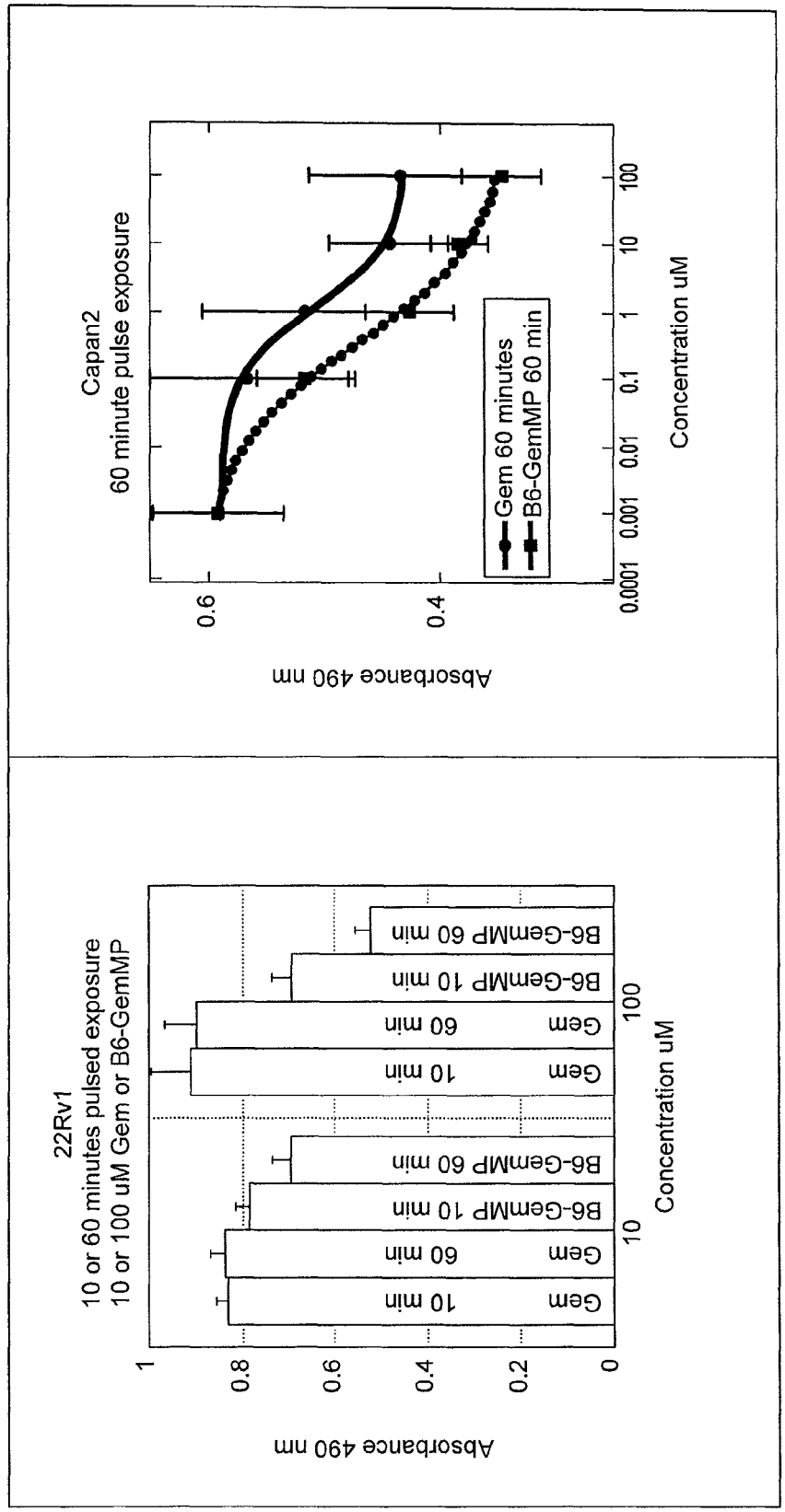
FIG. 2. Comparison of 10 or 60 minute pulsed exposure of pancreatic or prostate cancer cells to Gemcitabine or compound 16.

FIG. 1 illustrates the $B_6$-GemMP compound in pancreatic cell lines is 2-100-fold more potent than Gem alone (top row); and up to 7-fold more potent in the prostate cancer cell line 22Rv1. In addition, the $B_6$-araCMP compound appears >10-fold more potent than araC in 22Rv1 cells. Not all cell lines are more sensitive to the conjugates than the parent drug as shown in the PC3 prostate cancer line with Gem (sensitivity +3-fold). However, such cells are still responsive to the compounds on the same order as the parent drug and this highlights the fact that the conjugation has not blocked drug sensitivity; while still allowing for a novel cell uptake route.

In FIG. 2 the conjugates were designed to exploit alternative uptake mechanisms and provide the phosphorylated form of the nucleoside analogs they are derived from, thus potentially enabling a more rapid effect on the cells. This was tested for with a 10 or 60 minute pulsed exposure of 22Rv1 cells to compounds, followed by 48 hours of incubation in fresh media. As shown in FIG. 2 a pulse of as little as 10 minutes elicited measurable anti-proliferation in 22Rv1 cells with the conjugate only. In the case of the 100 uM pulse for 60 minutes the conjugate decreased proliferation 40% more than the free gemcitabine. Interestingly the 100 uM pulse of free gemcitabine stimulated proliferation 10% as was seen with the 48 hour exposure to lower concentrations (0.1-10 uM). In the Capan2 cells a trend is seen over all concentrations tested, again suggesting a more rapid effect in the case of the conjugate compared to the free Gem. The conjugates relatively greater potency with shorter cell exposure may be in part a function of providing the monophosphorylated drug form; however, the surprising observation of increased potency with as little as 10 minutes exposure to the conjugate, suggests the vitamin transporter may more rapidly move the conjugate into the cell relative to the traditional route of nucleoside uptake. It would be expected the predominant route of nucleoside uptake, the human equilibrative nucleoside transporter (hENT), would more slowly transport the conjugate (if at all) relative to the unconjugated nucleoside, and thus provides an unanticipated novel property of the vitamin-$B_6$ conjugation approach.

Figure 4:
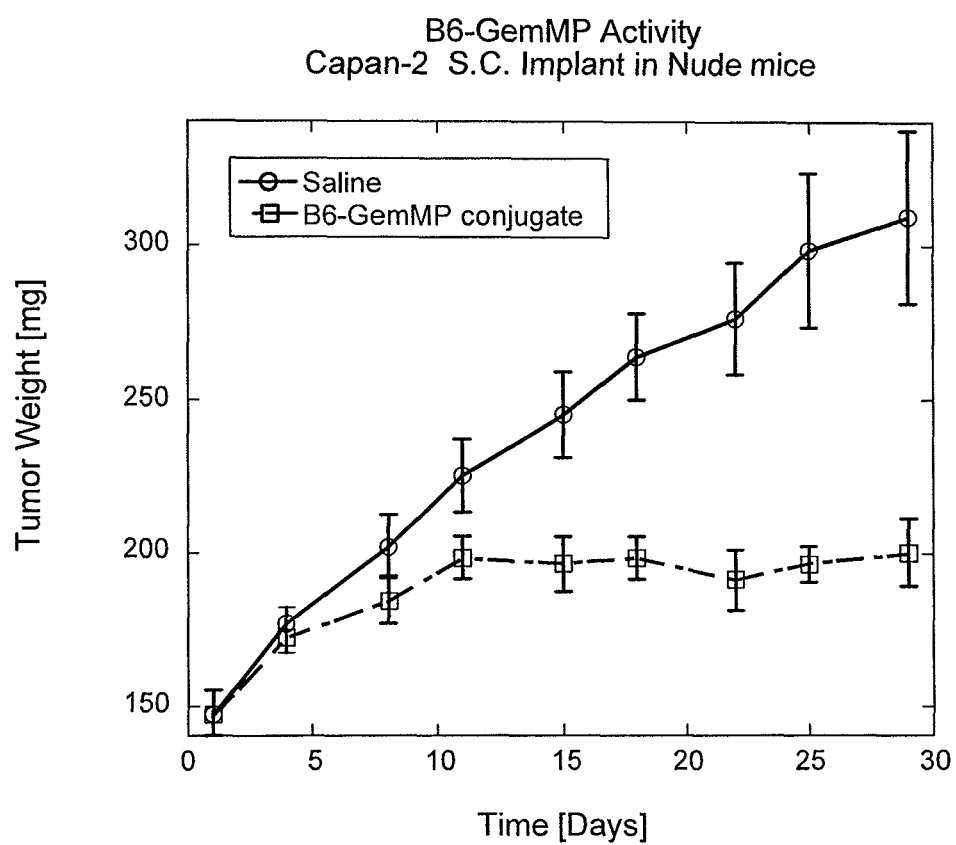
FIG. 4. Demonstration of in vivo efficacy in a mouse xenograft model of pancreatic cancer with compound 16 ($B_6$-GemMP).

FIG. 4 illustrates the conjugate of vitamin $B_6$ and gemcitabine is efficacious in a mouse model of human pancreatic cancer. In this model, immune compromised nude mice were injected subcutaneously with the human pancreatic cell line Capan-2 (~10^6 cells/100 ul). After tumor growth was

PUBLICATIONS

Stryer, L., "Flow of Genetic Information". Biochemistry, Fourth Ed., Ch. 5, pp. 95-97 (1995).

Stryer, L., "DNA and RNA: Molecules of Heredity", Biochemistry, Fourth Ed., Ch. 4. pp. 75, 76, 80-83 (1995).

Siddiqui et al., "Design and Synthesis of Lipophilic Phosphoramidate d4T-MP Prodrugs Expressing High Potency Against HIV in Cell Culture: Structural Determinants for in Vitro Activity and QSAR", J Med Chem 42 (1999), pp. 4122-4128.

Remy et al., "Studies on fluroinated pyrimidines. XIV. The synthesis of derivatives of 5-fluoro-2'-deoxyuridine 5'-phosphate and related compounds"; J Org Chem 27:2491-2500 (1962).

Lehsten et al., "An improved procedure for the synthesis of nucleoside amidates"; Organic Process Research & Development 6:819-822 (2002).

Juodka et al., "Oligonucleotides and nucleotide-peptide. XXXIV. Synthesis and some properties of complex nucleotidyl (oligonucleotidyl)-(P→N)-aminoacids (peptides) and their ethyl esters"; J Carbohydrates Nucleosides Nucleotides 6(4):333-357 (1979).

McGuigan et al., "Synthesis and Evaluation of some masked phosphate esters of the anti-herpesvirus drug 882C (Netivudine) as potential antiviral agents", Antiviral Chemistry & Chemotherapy 9:233-243 (1998).

Juodka et al., "Oligonucleotides and nucleotide-peptides. XXXVII. On the Mechanism of Hydrolysis of Uridylyl-(5' . . . N)-amino acids. Intramolecular catalysis by the α-carboxyl group of amino acids"; J Carbohydrates Nucleosides Nucleotides 8(6):519-535 (1981).

Negishi et al., "N4-Aminocytidine, a Nucleoside Analog that has an Exceptionally High Mutagenic Activity", Nucleic Acids Research 11(15):5223-5233 (1993).

Liorancaite et al., "Synthesis and Some Properties of Oligonucleotidyl-(Pm->N)-Serines", Nucleic Acids Symposium Series 9:215-18 (1981).

Zhou et al., "Simultaneous Formation of Peptides and Nucleotides from N-Phosphothreonine", Origins of Life and Evolution of the Bioshphere 26:547-560 (1996).

Gromova et al., "Optical Rotary Dispersion and Circular Dichroism of Mono- and Oligonucleotide-Amino Acids (Amidates)", Biochim Biophys Acta 240:1-11 (1971).

Joudka et al., "Oligonucleotides and Nucleotide-Peptides. XXXV. Some Properties of Nucleotidyl-(5'->N)-Amino Acid Esters Differing in Amino Acid and Nucleotide Components1)", J Carbohydrates Nucleosides Nucleotides 8 (1):19-39 (1981).

Abraham et al., "Synthesis and Biological Activity of Aromatic Amino Acid Phosphoramidates of 5-Fluoro-2'-deoxyuridine and 1-beta-Arabinofuranosylcytosine: Evidence of Phosphoramidase Activity", J Med Chem 39:4569-4575 (1996).

Sa Harris, et al., "Synthesis and antiviral evaluation of phosphoramidate derivatives of (E)-5-(2-bromovinyl)-2'-deoxyuridine", Antiviral Chemistry and Chemotherapy, vol. 12 (2001), pp. 293-300.

Edward J. McIntee, et al., "Amino Acid Phosphoramidate Nucleosides: Potential ADEPT/GDEPT Substrates", Bioorganic & Medicinal Chemistry Letters, 11 (2001), pp. 2803-2805.

Lisa J. Whalen, et al., "Synthesis and Evaluation of Phosphoramidate Amino Acid-Based Inhibitors of Sialyltransferases", Bioorganic & Medicinal Chemistry Letters, 13 (2003), pp. 301-304.

David B. Lackey, et al., "Enzyme-catalyzed therapeutic agent (ECTA) design: activation of the antitumor ECTA compound NB1011 by thymidylate synthase", Biochemical Pharacology, 61 (2001), pp. 179-189.

Harris et al., Antiviral Chemistry and Chemotherapy, vol. 12, 2001, pp. 293-300.

What is claimed is:

1. A compound having the general structure:

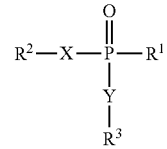

wherein $R^1$ is a substituent derived by removal of the hydrogen from the 5'-O-hydroxyl of a nucleoside or removal of an equivalent hydrogen from an acyclonucleoside;

X and Y are independently O, S, or NH; and $R^2$ and $R^3$ are independently selected from the group consisting of H, phenyl, alkyl, aryl, heteroaryl, and a vitamin $B_6$ moiety having one of the structures

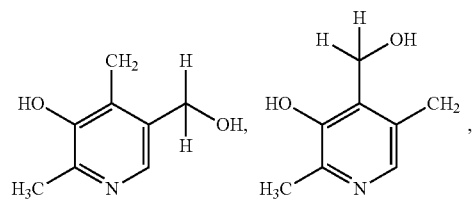

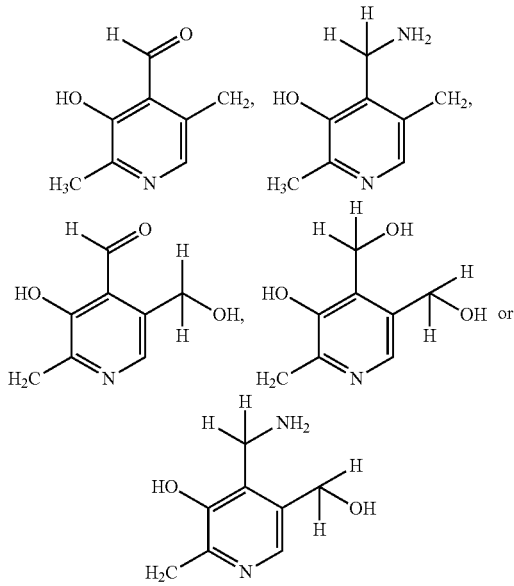

wherein at least one of $R^2$ and $R^3$ is a vitamin $B_6$ moiety.

2. The compound of claim 1, wherein $R^1$ is selected from the group consisting of:

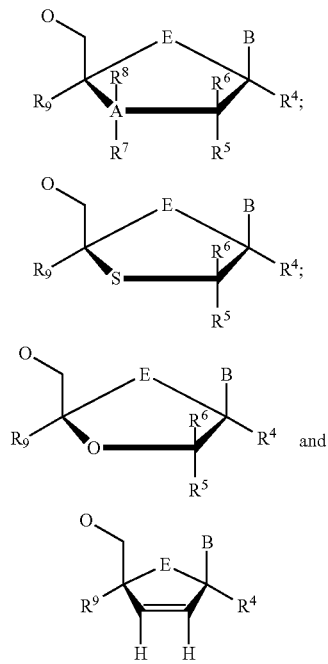

wherein B is a modified or unmodified nucleic acid base;
E is O, $CH_2$, NH, or S; and
$R^4$, $R^5$, $R^6$, $R^7$, $R^8$ and $R^9$ are independently selected from the group consisting of H, OH, F, $NH_2$, $N_3$, alkyl, alkenyl, and alkynyl.

3. The compound of claim 1, wherein $R^1$ is selected from the group consisting of:

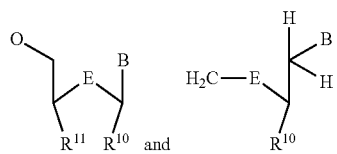

wherein B is a modified or unmodified nucleic acid base,
E is O or $CH_2$; and
$R^{10}$ and $R^{11}$ are independently selected from the group consisting of H, OH, F, $NH_2$, $N_3$, alkyl, alkenyl, and alkynyl.

4. A compound having the general structure:

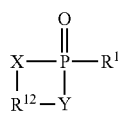

wherein $R^1$ is a substituent derived by removal of the hydrogen from the 5'-O-hydroxyl of a nucleoside or removal of an equivalent hydrogen from an acyclonucleoside;
X and Y are independently O, S, or NH; and
$R^{12}$ is a vitamin $B_6$ moiety having the following structure:

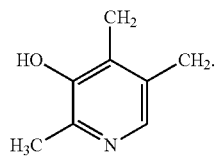

5. A compound having the general structure:

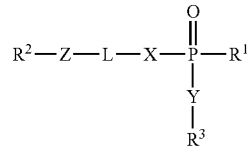

wherein $R^1$ is a substituent derived by removal of the hydrogen from the 5'-O-hydroxyl of a nucleoside or removal of an equivalent hydrogen from an acyclonucleoside;
X, Y and Z are independently O, S, or NH;
$R^2$ and $R^3$ are independently selected from the group consisting of H, phenyl, alkyl, aryl, heteroaryl, and a vitamin $B_6$ moiety having one of the structures

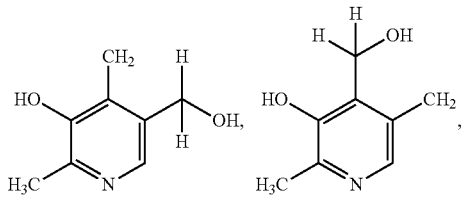

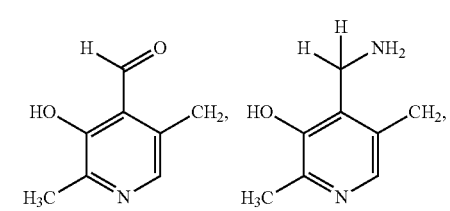

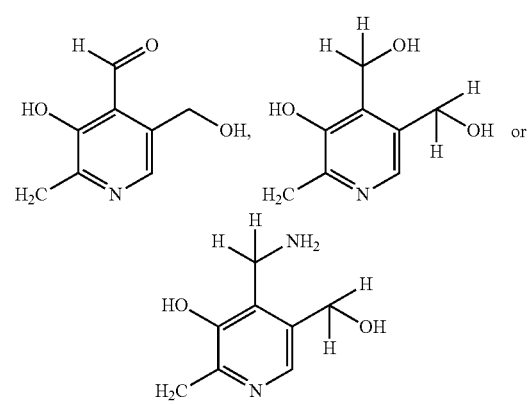

wherein at least one of $R^2$ and $R^3$ is a vitamin $B_6$ moiety; and

L is alkyl, alkenyl or alkynyl.

6. A compound having the general structure:

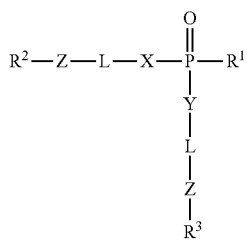

wherein $R^1$ is a substituent derived by removal of the hydrogen from the 5'-O-hydroxyl of a nucleoside or removal of an equivalent hydrogen from an acyclonucleoside;

X, Y and Z are independently O, S, or NH;

$R^2$ and $R^3$ are independently selected from the group consisting of H, phenyl, alkyl, aryl, heteroaryl, and a vitamin $B_6$ moiety having one of the structures

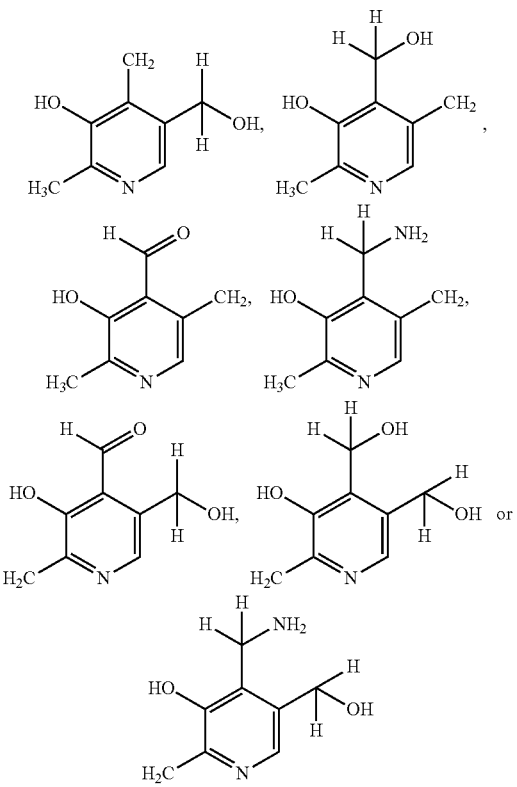

wherein at least one of $R^2$ and $R^3$ is a vitamin $B_6$ moiety; and

L is alkyl, alkenyl or alkynyl.

7. A pharmaceutical composition comprising a compound according to any one of claims 1, 4, 5, 6 and a pharmaceutically acceptable carrier, diluent, excipient, or a combination thereof.

8. A method of delivering a nucleoside-monophosphate, an acyclonucleoside-monophosphate, or acyclic nucleoside phosphonate into a cell, the method comprising administering one or more of the compounds of any one of claims 1, 4, 5, 6 to a host in need thereof.

9. The compound of any one of claims 1, 4, 5, 6, wherein $R^1$ is selected from the group consisting of:

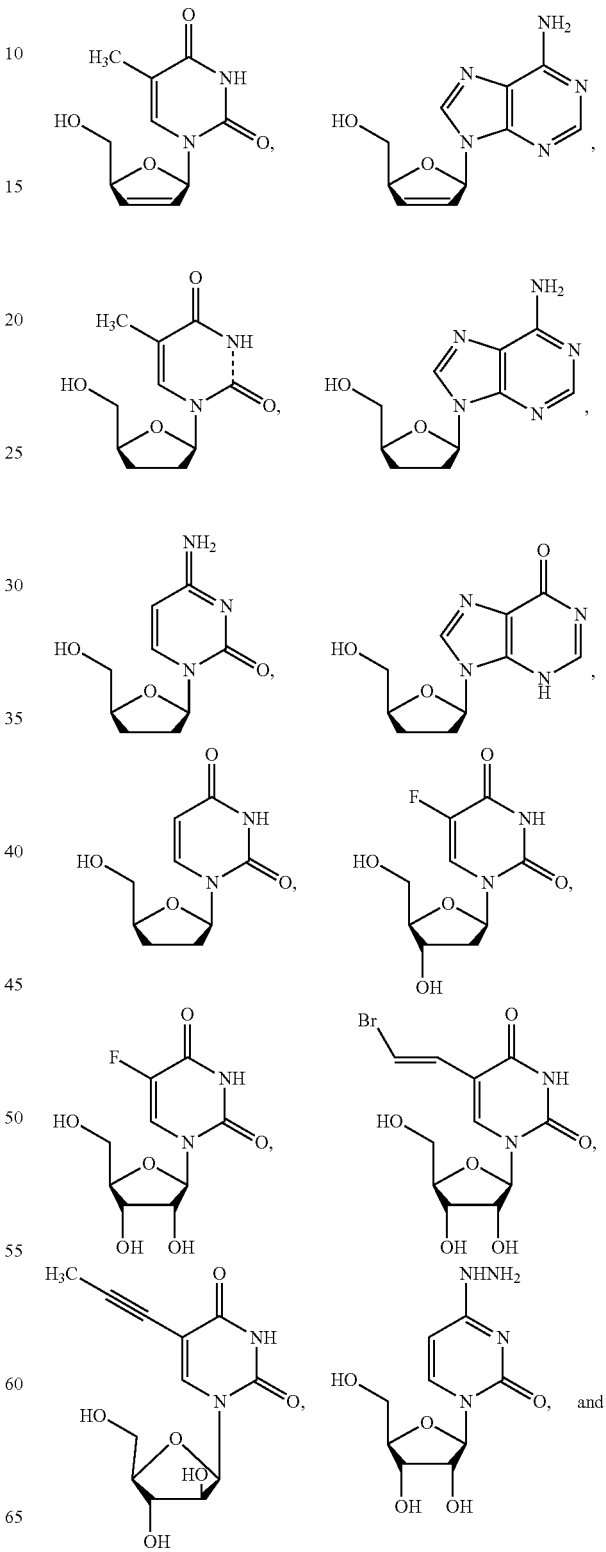

-continued
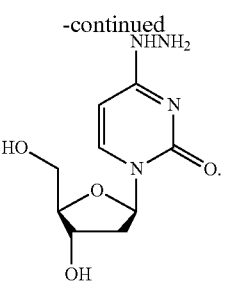
10. The compound of any one of claims 1, 4, 5, 6, wherein $R^1$ is selected from the group consisting of: cytarabine, fludarabine, gemcitabine, clofarabine, cladribine, vidaza, dacogen, pentostatin, aristeromycin, acyclovir, ganciclovir, pencyclovir, adefovir, cidofovir, tenofovir, zidovudine, lamivudine, and cladribine.
* * * * *